US006572603B1

(12) United States Patent
Tani et al.

(10) Patent No.: US 6,572,603 B1
(45) Date of Patent: Jun. 3, 2003

(54) VITAMIN D SOLUTION HOLDER AND CONTAINERS FOR TRANSFUSIONS

(75) Inventors: Seiji Tani, Tokushima (JP); Shigehito Sekimoto, Tokushima (JP); Junji Kaga, Tokushima (JP), JPN; Hideki Kobatake, Naruto (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 0 days.

(21) Appl. No.: 09/601,506

(22) PCT Filed: Jan. 29, 1999

(86) PCT No.: PCT/JP99/00386

§ 371 (c)(1),
(2), (4) Date: May 24, 1999

(87) PCT Pub. No.: WO99/39679

PCT Pub. Date: Dec. 8, 1999

(30) Foreign Application Priority Data

Feb. 3, 1998 (JP) ........................................ 10-022271

(51) Int. Cl.[7] ........................................ A61B 19/00
(52) U.S. Cl. .................................... 604/403; 604/403
(58) Field of Search ............................. 604/403–416; 424/451, 455; 552/653; 426/72–73, 167

(56) References Cited

U.S. PATENT DOCUMENTS

| | | | | | |
|---|---|---|---|---|---|
| 4,997,083 | A | * | 3/1991 | Loretti et al. | 206/219 |
| 5,385,737 | A | * | 1/1995 | Shigeno et al. | 264/4.3 |
| 5,423,421 | A | * | 6/1995 | Inoue et al. | 206/219 |
| 5,425,447 | A | * | 6/1995 | Farina | 206/219 |
| 5,738,871 | A | * | 4/1998 | Story | 424/451 |
| 5,925,381 | A | * | 7/1999 | Boyle et al. | 424/484 |

FOREIGN PATENT DOCUMENTS

JP 8-191873 7/1996 ............. A61J/1/05

OTHER PUBLICATIONS

Patent abstract of Japan, 08191873. 07/30/96.
International Search Report.

* cited by examiner

*Primary Examiner*—Angela D. Sykes
*Assistant Examiner*—Leslie Deak

(57) ABSTRACT

The present invention relates to a polyolefin-made holder for solutions containing vitamin D or derivatives thereof, in which the volume of polyolefin constituting a solution-holding portion of the holder is 30 $cm^3$ or less per $\mu$mol of the vitamin D or derivatives thereof contained therein; and to a transfusion fluid container comprising the vitamin D solution holder. Use of the holder or container can minimize reduction in vitamin D content.

20 Claims, 2 Drawing Sheets

A-A cross sectional view

VITAMIN D SOLUTION HOLDER AND CONTAINERS FOR TRANSFUSIONS

TECHNICAL FIELD

The present invention relates to a polyolefin-made holder for a vitamin D solution, which minimizes reduction in vitamin D content, and to a transfusion fluid container that accommodates the holder.

BACKGROUND ART

In many cases, patients who have undergone surgery on the digestive tract cannot ingest nutrition orally. Therefore, in order to provide nutrition to such patients, intravenous hyperalimentation (IVH) is generally carried out. IVH facilitates an improvement in the nutritional status of the aforementioned patients and maintenance of the improved nutritional status, and thus promotes recovery and healing in these patients. Therefore, IVH is considered to be very effective, and at present IVH is widely employed in the field of surgical treatment.

In IVH, carbohydrates and amino acids, serving as nutritional sources, and electrolytes are usually administered. Transfusion products containing all of these sources have been developed for IVH, and generally, commercially available products are of the type in which two containers, one containing glucose and the other containing amino acids (here the glucose and amino acids are known to induce the Maillard reaction).

When IVH is carried out for a relatively prolonged period of time, problems can arise. For example, lack of trace elements and vitamins which are not contained in the transfusion products may lead to malnutrition. Particularly, vitamin $B_1$ is consumed in glucose metabolism, and thus tends to be lacking, inducing grave acidosis. Therefore, when IVH is prolonged beyond a certain short period of time (e.g., approximately one week), vitamins must be co-administered. Due to the unstable nature of vitamins, vitamins are formulated singly and supplied in the form of a vitamin mixture or a multi-vitamin preparation, and such vitamins are mixed with an IVH product in a clinical setting, such as a hospital, at the time of use. However, carrying out such a mixing operation in a hospital is cumbersome. In addition, the IVH product may become contaminated with bacteria during the mixing process, and thus the operation requires efficiency and care. This imposes an excessive workload on the person who administers IVH.

In order to make the aforementioned mixing operation more convenient, attempts have been made to produce a two-container-type IVH product which incorporates the vitamins. For example, fat and sugar are contained in one of two containers, amino acids and electrolytes are contained in the other, and a variety of vitamins can then be incorporated into either of the two containers (Japanese Patent Application Laid-Open Nos. 6-209979 and 8-709).

Fat, which is an important component of nutrition, is also incorporated into IVH products. However, fat must not be administered to patients suffering hyperlipidemia, liver dysfunction, thrombosis, or diabetic ketosis. Suitable dosage of fat may vary among patients, and in some cases, it may be preferable to administer fat alone.

However, in the aforementioned IVH product, particular vitamins are stabilized by incorporation of fat, and thus, maintaining the stability of vitamins (e.g., vitamin $B_2$) without fat is difficult.

In general, transfusion fluid containers which are produced from polyolefin, such as polyethylene or polypropylene, are widely employed, since such containers are easy to shape and are considered safe. However, when a solution containing vitamin D among other vitamins is stored in the aforementioned polyolefin-made container for a prolonged period of time, the vitamin D is adsorbed into the container and the vitamin content of the solution is lowered considerably. As a result, malabsorption of calcium, or bone embrittlement due to vitamin D deficiency may arise in patients who have undergone transfusion of fluids that have been stored in such containers.

Studies have been carried out on a variety of kit-type transfusion fluid containers in which holders containing substances such as vitamins are separately prepared and the holders are connected to the containers. For example, Japanese Patent Application Laid-Open (kokai) No. 6-54889 discloses a bag assembly in which syringes are connected. In such transfusion fluid containers, when holders for containing drugs are produced from a material which does not adsorb vitamin D, such as glass, the aforementioned problem can be avoided. However, the holders can be associated with higher production costs, and dismantling of the holders for separate disposal after use can be laborious.

In view of the foregoing, an object of the present invention is to provide a polyolefin-made holder for a vitamin D solution, which minimizes any reduction in vitamin D content, and a transfusion fluid container incorporating the holder.

DISCLOSURE OF THE INVENTION

In order to solve the aforementioned problems, the present inventors have performed extensive studies and have found that even when polyolefin, which adsorbs vitamin D, is employed in a holder, reduction in vitamin D content can be limited to an acceptable range when the volume of polyeolefin constituting a solution-holding portion of the holder is a predetermined amount or less. The present invention has been accomplished on the basis of this finding.

Accordingly, the present invention provides a polyolefin-made holder for a vitamin D solution containing vitamin D or a derivative thereof, wherein the volume of polyolefin constituting the solution-holding portion of the holder is 30 $cm^3$ or less per $\mu$mol of the vitamin D or derivatives thereof.

The present invention also provides a transfusion fluid container, which is flexible and accommodates the holder for the vitamin D solution.

BEST MODE FOR CARRYING OUT THE INVENTION

Figure 1:
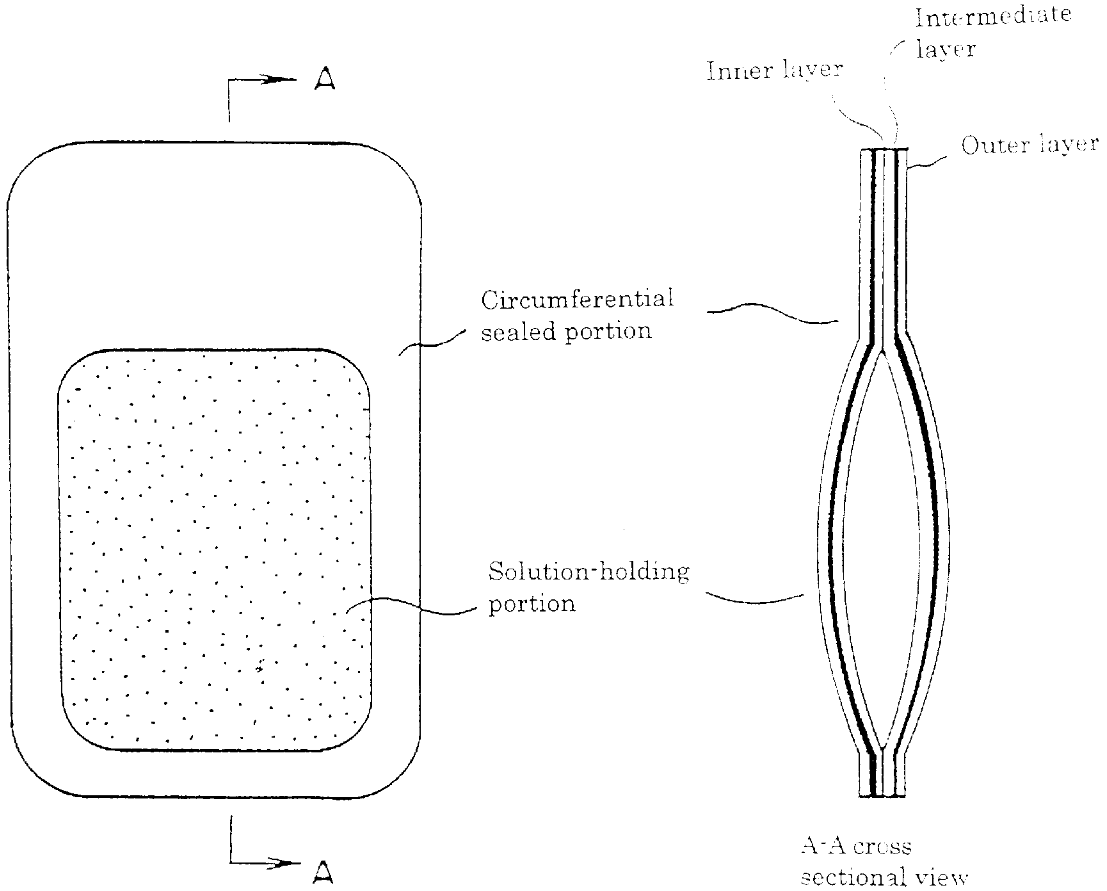
FIG. 1 is a schematic representation showing an embodiment of the holder for a vitamin D solution of the present invention.

The holder of the present invention contains a solution containing vitamin D or derivatives thereof. Examples of vitamin D or derivatives thereof include vitamin $D_1$, vitamin $D_2$, vitamin $D_3$ (cholecalciferol), and active forms thereof (hydroxy derivatives).

The solution in the holder of the present invention may contain, in addition to vitamin D or derivatives thereof, fat-soluble vitamins such as vitamin A, vitamin E, and vitamin K; water-soluble vitamins; and electrolytes.

When the solution contains a fat-soluble vitamin, the vitamin is preferably made soluble by employment of a surfactant. Examples of surfactants which may be employed include polyoxyethylene sorbitan fatty acid esters (commercially available products such as Tween 80 and Tween 20), polyoxyethylene hydrogenated castor oil (commercially available products such as HCO60), and ethylene glycol.propylene glycol block copolymers (commercially available products such as Pluronic F68). These surfactants are usually employed in the solution in an amount of 0.1–100 g/l.

In addition, when the solution contains vitamin C or reducing agents, including sulfites, hydrogensulfites, or thiols such as cysteine, the stability of the solution may be enhanced.

The holder of the present invention is produced from polyolefin. The species of polyolefin is not particularly limited, so long as it may be employed in a conventional clinically-used holder. Examples of such a polyolefin include chain olefin polymers such as polyethylene, polypropylene, poly(1-butene), and poly(4-methyl-1-pentene).

Of these, the polyethylene may be an ethylene homopolymer or a copolymer of ethylene and α-olefins, such as propylene, 1-butene, or 4-methyl-1-pentene. The copolymer may be in the form of a linear or branched chain. In the present invention, the polyethylene may be of either high or low density, and thus may be chosen from a variety of forms. With respect to softness and transparency, linear low-density polyethylene is preferable.

The polypropylene may be a propylene homopolymer, or a copolymer of propylene and small amounts (generally 10 wt. % or less, preferably 5 wt. % or less) of olefins, such as ethylene and 1-butene. The propylene to be employed is preferably high-grade polypropylene which is widely used for producing clinical holders.

These polyolefins may be used singly or in combination as a mixed resin.

The holder of the present invention can be produced by sealing the periphery of films of the aforementioned polyolefin and shaping the bag by employment of conventional methods.

The volume of resin in the solution-holding portion of the holder—i.e., the portion other than the sealed peripheral portion—with which the solution is brought into contact is 30 $cm^3$ or less, preferably 20 $cm^3$ or less, more preferably 10 $cm^3$ or less per μmol of vitamin D or derivatives thereof in the solution. When the volume is in excess of 30 $cm^3$, adsorption of vitamin D cannot be suppressed.

The aforementioned volume of resin can be calculated by multiplying the surface area of the solution-holding portion of the holder by the thickness of the portion.

The thickness of a polyethylene-made film is 100 μm or less, preferably 20–50 μm.

The holder of the present invention may be produced from a monolayer film of polyolefin as described above, or from a multi-layered film comprising a polyolefin layer on which is formed a resin layer which absorbs substantially no vitamin D. Examples of resins which do not adsorb vitamin D include polyethylene terephthalate, polyethylene naphthalate, polyacrylonitrile, polyamides (e.g., nylon), polycarbonates, poly(ethylene fluoride), and cyclic olefin copolymers. Generally, thermal welding of these resins is difficult, but a multi-layer film comprising polyolefin as the innermost layer is easily shaped into a holder.

A specific example of such a multi-layer film is a three-layer film comprising inner and outer layers formed of polyethylene and an intermediate layer of nylon (FIG. 1).

Another specific example is preferably a three-layer film comprising inner and outer layers formed of polyolefin, such as polyethylene or polypropylene, and an intermediate layer formed of a cyclic olefin copolymer. An example of such cyclic olefin copolymer is a commercially available ethylene.tetracyclododecene copolymer. Such copolymers may be employed as raw materials for the aforementioned film.

When such a multi-layer film is employed in a holder, in the same manner as a polyolefin monolayer film, the volume of polyolefin constituting the innermost layer of the multi-layered film, which corresponds to the solution-holding portion, is 30 $cm^3$ or less, preferably 20 $cm^3$ or less, more preferably 10 $cm^3$ or less per μmol of vitamin D or derivatives thereof in a solution contained in the holder.

The thickness of the polyolefin layer (the innermost layer) with which a solution is brought into contact is 100 μm or less, preferably 5–50 μm.

The holder for a vitamin D solution of the present invention may be produced singly as a final product. Alternatively, the holder may be incorporated into the inside of a flexible transfusion fluid container. The present invention encompasses such a transfusion fluid container.

In order to accommodate the holder into a transfusion fluid container, the holder may be floated in the solution in the container. Preferably, an edge of the peripheral sealed portion of the holder for the vitamin D solution is sandwiched between peripheral portions of the container and sealed, to thereby affix the edge of the holder to the container. In this case, in order to carry out sealing, the material of the container is preferably the same as that of the holder of the vitamin D solution or that of the outermost layer of the holder.

Preferably, the above-described holder for the vitamin D solution includes an easily opened seal or is produced from a film having a thickness of 100 μm or less, such that the holder can be opened or broken manually when a transfusion fluid container that includes the holder is set up for administration.

Figure 2:
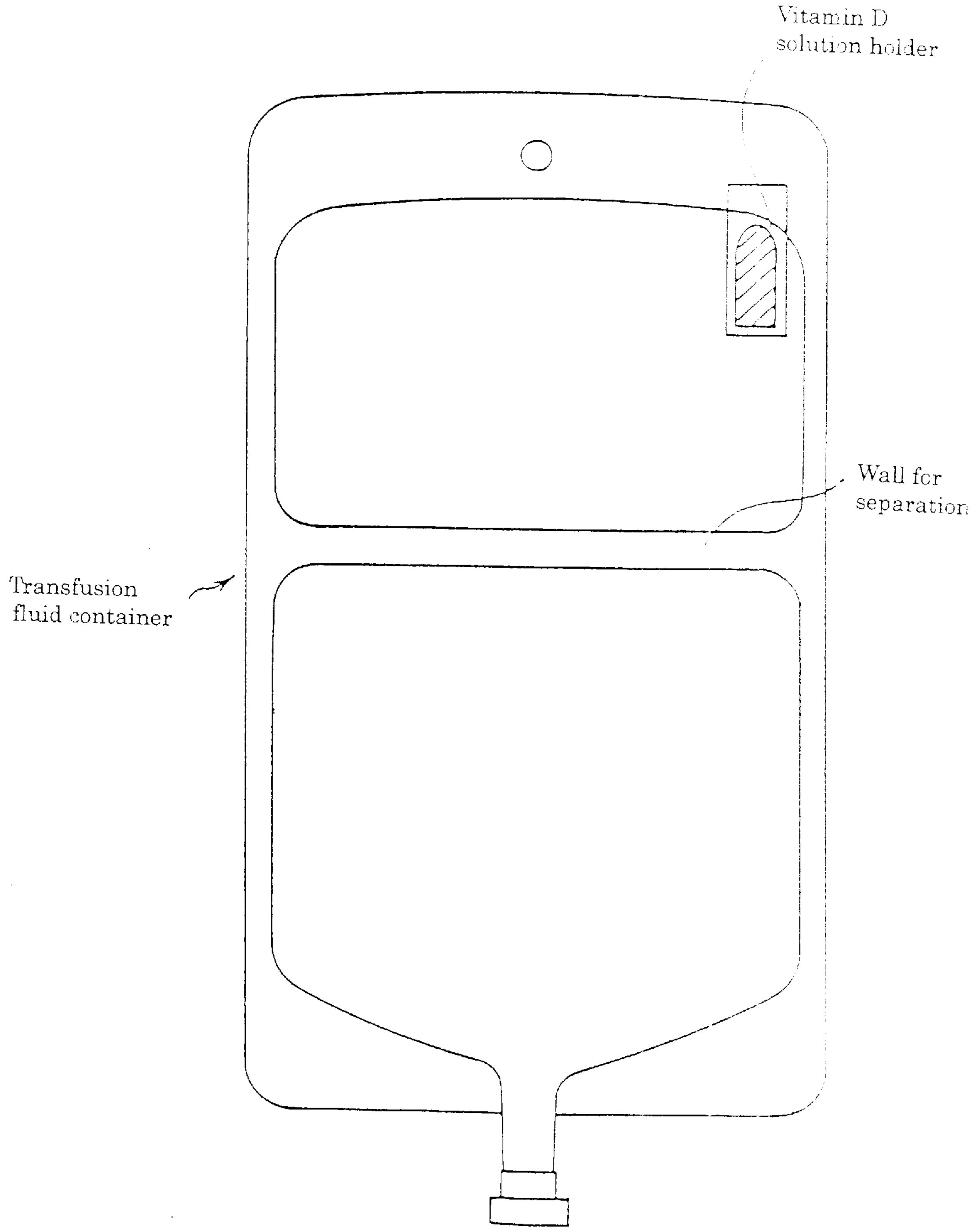
FIG. 2 is a schematic representation showing an embodiment of the transfusion fluid container of the present invention.

A specific example of such a transfusion fluid container comprises two compartments divided by a partition which allows fluid communication therethrough, in which solution (B) containing amino acids is contained in one compartment, solution (A) containing reducing sugar is contained in the other, and electrolytes and other vitamins are appropriately contained in either of the two compartments. The holder for the vitamin D solution can be incorporated into either of the compartments (FIG. 2).

The above-described transfusion fluid container preferably contains solution (A) containing vitamin $B_1$, solution (B) containing folic acid, and the vitamin D solution containing other fat-soluble vitamins and vitamin C, in which vitamin $B_2$ is incorporated into solution (B) or the vitamin D solution and the pHs of solution (A), solution (B), and the vitamin D solution are adjusted to 3.5–4.5, 5.0–7.0, and 5.5–7.0, respectively.

Preferably, solution (A) further contains a pantothenic acid derivative, and the vitamin D solution contains vitamin $B_2$, and more preferably, solution (B) contains vitamin $B_{12}$.

Particularly preferably, solution (A) further contains vitamin $B_6$, solution (B) further contains a nicotinic acid derivative, and the vitamin D solution further contains biotin.

A preferable example of the above-described transfusion fluid container will next be described in more detail.

Examples of reducing sugars which may be incorporated into solution (A) include glucose, fructose, and maltose. Of these, glucose is particularly preferable, in consideration of blood sugar control. Solution (A) may contain non-reducing sugars such as xylitol, sorbitol, and glycerin.

Reducing sugars may be incorporated in solution (A) singly or in combination of two or more species, and when incorporated they are incorporated into solution (A) in an amount of 120–450 g/l, preferably 150–300 g/l.

Solution (A) further contains vitamin $B_1$. In order to stabilize vitamin $B_1$, the pH of solution (A) is adjusted to 3.5–4.5, preferably 3.8–4.2. A variety of organic acids, inorganic acids, organic bases, and inorganic bases, which are usually employed, may appropriately be employed for adjustment of the pH.

Vitamin $B_1$ is incorporated into a half-day or daily dose of solution (A) in an amount of 1–12 mg, particularly preferably 1.5–8 mg. Examples of vitamin $B_1$s (thiamins) which may be employed include thiamin hydrochloride, thiamin nitrate, prosulthiamin, and octothiamin. In order to prevent decomposition of vitamin $B_1$, preferably, substantially no sulfites or hydrogensulfites are incorporated into solution (A) containing vitamin $B_1$.

Examples of amino acids which may be incorporated into solution (B) include essential amino acids and nonessential amino acids, such as L-isoleucine, L-leucine, L-lysine, L-methionine, L-phenylalanine, L-threonine, L-tryptophan, L-valine, L-alanine, L-arginine, L-aspartic acid, L-cysteine, L-glutamic acid, L-histidine, L-proline, L-serine, L-tyrosine, and glycine. These amino acids are preferably purely crystalline amino acids. These amino acids usually take the form of free amino acid, but may take other forms. For example, these amino acids may take forms of pharmaceutically acceptable salts, esters, N-acyl derivatives, salts of two amino acid species, and peptides.

The preferable amounts of these amino acids (on the basis of free form) which are contained in solution (B) are as follows.

TABLE 1

| | |
|---|---|
| L-Isoleucine | 3.0–12.0 g/l |
| L-Leucine | 6.0–21.0 g/l |
| L-Lysine | 4.5–22.5 g/l |
| L-Methionine | 1.5–7.5 g/l |
| L-Phenylalanine | 3.0–12.0 g/l |
| L-Threonine | 2.4–9.0 g/l |
| L-Tryptophan | 0.6–3.6 g/l |
| L-Valine | 2.1–12.6 g/l |
| L-Alanine | 3.0–12.6 g/l |
| L-Arginine | 4.2–16.5 g/l |
| L-Aspartic acid | 0.3–5.1 g/l |
| L-Cysteine | 0.3–2.1 g/l |
| L-Glutamic acid | 0.3–9.0 g/l |
| L-Histidine | 2.4–8.1 g/l |
| L-Proline | 1.8–7.8 g/l |
| L-Serine | 0.9–5.1 g/l |
| L-Tyrosine | 0–1.5 g/l |
| Glycine | 3.0–13.5 g/l |

Solution (B) further contains folic acid, and the pH of the solution is adjusted to 5.5–7.5, preferably 6.0–7.0. A variety of organic acids, inorganic acids, organic bases, and inorganic bases, which are usually employed, may appropriately be employed for adjustment of pH. Folic acid is incorporated into a half-day or daily dose of solution (B) in an amount of 0.1–1 mg, particularly preferably 0.1–0.7 mg.

Examples of fat-soluble vitamins which may be incorporated into the vitamin D solution include vitamin A, vitamin D, and vitamin E. If necessary, the solution may contain vitamin K. Vitamin A (retinol) may take the form of an ester such as palmitate or acetate. Vitamin D may be vitamin $D_1$, vitamin $D_2$, vitamin $D_3$ (cholecalciferol), or active forms of these (hydroxy derivatives). Vitamin E (tocopherol) may take the form of an ester such as acetate or succinate. Vitamin K (phytonadione) may be a derivative of menatetrorenone or menadione.

These fat-soluble vitamins are incorporated into a half-day or daily dose of the vitamin D solution in the following amounts. The amount of vitamin A is 1,250–5,000 IU, preferably 1,400–4,500 IU; the amount of vitamin D is 10–1,000 IU, preferably 50–500 IU; the amount of vitamin E (tocopherol) is 2–20 mg, preferably 3–15 mg; and the amount of vitamin K is 0.2–10 mg, preferably 0.5–5 mg.

These fat-soluble vitamins are preferably solubilized in water by use of a surfactant. Examples of surfactants which may be employed include polyoxyethylene sorbitan fatty acid esters (commercially available products such as Tween 80 and Tween 20), polyoxyethylene hydrogenated caster oil (commercially available products such as HCO60), and ethylene glycol.propylene glycol block copolymers (commercially available products such as Pluronic F68). These surfactants are employed in a solution usually in an amount of 10–1,000 mg/l.

The vitamin D solution further contains vitamin C, and the pH of the solution is adjusted to 5.5–7.5, preferably 6.0–7.0. A variety of organic acids, inorganic acids, organic bases, and inorganic bases, which are usually employed, may appropriately be employed for adjustment of pH.

Vitamin C (ascorbic acid) may take the form of sodium salt. Vitamin C is incorporated into a half-day or daily dose of the vitamin D solution in an amount of 20–250 mg, preferably 30–150 mg.

Vitamin $B_2$ is incorporated into solution (B) or the vitamin D solution.

Vitamin $B_2$ (riboflavin) may take the form of a phosphate, a sodium salt thereof, or flavin mononucleotide. Vitamin $B_2$ is incorporated into a half-day or daily dose of solution (B) or the vitamin D solution in an amount of 1–10 mg, particularly preferably 2–7 mg. Particularly, vitamin $B_2$ is preferably incorporated into the vitamin D solution.

In the transfusion fluid container of the present invention, each of the two compartments may further contain other vitamins.

For example, solution (A) may further contain a pantothenic acid derivative. This vitamin; i.e., the derivative, may be incorporated into both of solution (A) and solution (B), but is preferably incorporated into only solution (A), in consideration of enhancement of stability. The pantothenic acid derivative may take a free form or the form of calcium salt or panthenol, which is a reduced product of pantothenic acid. The pantothenic acid derivative is incorporated into a half-day or daily dose of solution (A) in an amount of 1–30 mg, preferably 5–20 mg.

Solution (B) may further contain vitamin $B_{12}$. This vitamin may be incorporated into both of solution (A) and solution (B), but is preferably incorporated into only solution (B), in consideration of enhancement of stability. Preferably, vitamin $B_{12}$ is incorporated separately from vitamin C.

Vitamin $B_{12}$ is incorporated into a half-day or daily dose of solution (B) in an amount of 1–30 $\mu$g, preferably 2–10 $\mu$g.

Solution (A), solution (B), and the vitamin D solution may further contain vitamin $B_6$, a nicotinic acid derivative, and biotin, respectively. These vitamins may be incorporated into any of these solutions, but are preferably incorporated into the respective solutions as described above, in consideration of convenience of production.

Vitamin $B_6$ is incorporated into a half-day or daily dose of solution (A) in an amount of 1–10 mg, preferably 1.5–7 mg. Vitamin $B_6$ (pyridoxine) may take the form of a salt such as pyridoxine hydrochloride.

The nicotinic acid derivative is incorporated into a half-day or daily dose of solution (B) in an amount of 5–50 mg, preferably 10–45 mg. The nicotinic acid derivative may take a free form or the form of an amide, sodium salt, or methyl ester.

Biotin is incorporated into a half-day or daily dose of the vitamin D solution in an amount of 0.01–0.3 mg, preferably 0.01–0.1 mg.

In the transfusion fluid container of the present invention, each of the two compartments may further contain electrolytes, and electrolytes may be incorporated into any of solution (A), solution (B), and the vitamin D solution. No particular limitation is imposed on the species of electrolytes, so long as they can be employed in a customary electrolytic transfusion fluid. Examples of such electrolytes include sodium, potassium, calcium, magnesium, phosphorous, chlorine, and zinc. For example, hydrates and anhydrides of the following compounds may be employed in the above solutions.

Examples of sodium sources include sodium chloride, sodium acetate, sodium citrate, sodium dihydrogenphosphate, disodium hydrogenphosphate, sodium sulfate, and sodium lactate. Such a sodium source is preferably incorporated into any of the above solution so as to attain an amount of 25–70 mEq/l after mixing of all fluids in the solution.

Examples of potassium sources include potassium chloride, potassium acetate, potassium citrate, potassium dihydrogenphosphate, dipotassium hydrogenphosphate, potassium sulfate, and potassium lactate. Such a potassium source is preferably incorporated into any of the above solutions so as to attain an amount of 15–50 mEq/l after mixing.

Examples of calcium sources include calcium chloride, calcium gluconate, calcium pantothenate, calcium lactate, and calcium acetate. Such a calcium source is preferably incorporated into any of the above solutions so as to attain an amount of 3–15 mEq/l after mixing.

Examples of magnesium sources include magnesium sulfate, magnesium chloride, and magnesium acetate. Such a magnesium source is preferably incorporated into any of the above solutions so as to attain an amount of 3–10 mEq/l after mixing.

Examples of phosphorous sources include sodium dihydrogenphosphate, disodium hydrogenphosphate, and sodium glycerophosphate. Such a phosphorous source is preferably incorporated into any of the above solutions so as to attain an amount of 5–20 mmol/l after mixing.

Examples of chlorine sources include sodium chloride, potassium chloride, calcium chloride, and magnesium chloride. Such a chlorine source is preferably incorporated into any of the above solutions so as to attain an amount of 25–70 mEq/l after mixing.

Examples of zinc sources include zinc chloride and zinc sulfate. Such a zinc source is preferably incorporated into any of the above solutions so as to attain an amount of 0–30 μmol/l after mixing.

Of these electrolytes, calcium salts and magnesium salts are preferably incorporated into the above solution separately from phosphorous compounds. Other electrolytes may be incorporated into any of the above solutions without limitation.

Solution (B) may contain sulfites and/or hydrogensulfites as a stabilizer. Such a stabilizer is incorporated into solution (B) in an amount of 200 mg/l or less, preferably 100 mg/l or less.

In many cases, the transfusion fluid container of the present invention contains a half-day or daily dose of the fluid, and thus the vitamin D solution holder generally has a volume of 1–20 ml.

In general, the transfusion fluid container is contained in a gas-barrier wrapping bag together with a deoxidizing agent, in order to prevent oxidation decomposition of amino acids. If necessary, the bag is filled with inert gas during wrapping. When the container contains photodecomposable vitamins, the wrapping bag preferably has light-shielding ability.

Generally-used films or sheets formed from various substances may be used as a material of a gas-barrier wrapping bag which is suitable for wrapping. Examples of such materials include films or sheets containing at least one species selected from among ethylene-vinyl alcohol copolymers, polyvinylidene chloride, polyacrylonitrile, polyvinyl alcohol, polyamide, and polyester. When light-shielding ability is imparted to a wrapping bag, the aforementioned film or sheet may be subjected to, for example, aluminum lamination.

Examples of deoxidizing agents which may be employed include known deoxidizing agents containing, as an active ingredient, iron compounds such as iron hydroxide, iron oxide, and iron carbide. For example, commercially available ones, such as "Ageless" (product of Mitsubishi Gas Chem. Co., Inc.), "Modulan" (product of Nippon Kayaku Co., Ltd.), and "Secule" (product of Nippon Soda Co., Ltd.), may be employed.

If necessary, the transfusion fluid container of the present invention may optionally contain other agents such as trace elements,(e.g., iron, manganese, copper, and iodine) and antibiotics upon administration, so long as they do not induce any change in the transfusion fluid.

EXAMPLES

The present invention will next be described in more detail by way of examples, which should not be construed as limiting the invention thereto.

Example 1

Glucose and electrolytes were dissolved in distilled water for injection, and the pH of the resultant solution was adjusted to 4 by use of acetic acid, to thereby prepare a sugar electrolytic solution. Separately, vitamin $B_1$ (thiamin hydrochloride), vitamin $B_6$ (pyridoxine hydrochloride), and biotin were dissolved in distilled water for injection, and the resultant solution was mixed with the above-prepared sugar electrolytic solution. The mixture was filtered aseptically, to thereby prepare solution (A) having the composition shown in Table 2.

Crystalline amino acids, vitamin $B_{12}$ (cyanocobalamin), nicotinamide, panthenol, and electrolytes were dissolved in distilled water for injection, and the pH of the solution was adjusted to 6 by use of acetic acid. To the resultant solution, folic acid was added, and the mixture was filtered aseptically, to thereby prepare solution (B) having the composition shown in Table 2. To solution (B), sodium hydrogensulfite was added as a stabilizer so as to attain a concentration of 50 mg/l.

Separately, vitamin A (retinol palmitate), vitamin $D_3$ (cholecalciferol), vitamin E (tocopherol acetate), and vitamin K (phytonadione) were solubilized with polysolvate 80 (concentration in solution (C)=10 g/l) and polysolvate 20 (concentration in solution (C)=2 g/l). Thereafter, the solubilized vitamins were dissolved in distilled water for injection. In addition, vitamin $B_2$ (sodium riboflavin phosphate) and vitamin C (ascorbic acid) were added to the resultant solution, and the pH of the mixture was adjusted to 6 by use of sodium hydroxide. The resultant mixture was filtered aseptically, to thereby prepare solution (C) having the composition shown in Table 2.

In a holder produced from a polyethylene film having a thickness of 30 μm, solution (C) (4 ml) was charged and the inlet was melt-sealed, to thereby obtain a holder for the solution containing vitamin $D_3$. The surface area of a solution-holding portion of the holder was 16 $cm^2$ and the volume of polyethylene constituting the solution-holding portion was 0.048 $cm^3$.

100 IU of vitamin $D_3$ corresponds to 2.5 μg; i.e., 0.0065 μmol, and thus the volume of the polyethylene per μmol of vitamin $D_3$ in the solution was 7.4 $cm^3$.

In a polyethylene-made two-compartment container (see FIG. 2), the above-described holder for vitamin $D_3$ solution had been previously attached to one of the compartments. Solution (A) (600 ml) and solution (B) (300 ml) were charged into two compartments separately in an atmosphere replaced with nitrogen, and the container was sealed. Subsequently, the container was subjected to autoclaving through a customary method, to thereby obtain a transfusion product. The transfusion product was wrapped in a light-shielding nylon multi-layer bag together with a deoxidizing agent (trade name: Ageless, product of Mitsubishi Gas Chem. Co., Inc.).

Example 2

In the same manner as in Example 1, solution (A), solution (B), and solution (C), having the compositions shown in Table 2, were prepared, and these solutions were charged into a holder and two compartments of a transfusion fluid container as described in Example 1. Subsequently, the container was subjected to autoclaving, to thereby obtain a transfusion product. The transfusion product was wrapped in a light-shielding nylon multi-layer bag together with a deoxidizing agent (trade name: Ageless, product of Mitsubishi Gas Chem. Co., Inc.).

In a polyethylene-made vitamin $D_3$ solution holder containing solution (C), the surface area of a solution-holding portion was 16 $cm^2$ and the thickness of the portion was 150 μm. The volume of polyethylene constituting the solution-holding portion was 0.24 $cm^3$, and the volume of the polyethylene per μmol of vitamin $D_3$ in the solution was 18.5 $cm^3$.

In Examples 1 and 2, adsorption of vitamin $D_3$ was suppressed even after four-month storage, and the content of vitamin $D_3$ fell within an acceptable range (≧80%). The contents of other vitamins also fell within acceptable ranges.

TABLE 2

| | Ingredient | Example 1 | Example 2 |
|---|---|---|---|
| Solution (A) | Glucose | 292 g/l | 292 g/l |
| | Sodium chloride | 2.83 g/l | 2.83 g/l |
| | Magnesium sulfate | 1.23 g/l | 1.23 g/l |
| | Calcium chloride | 0.73 g/l | 0.73 g/l |
| | Zinc sulfate | 9.6 mg/l | 9.6 mg/l |
| | Thiamin hydrochloride ($B_1$) | 3.25 mg/l | 6.5 mg/l |
| | Pyridoxine hydrochloride ($B_6$) | 4.08 mg/l | 8.16 mg/l |
| | Biotin | 0.05 mg/l | 0.1 mg/l |
| Solution (B) | Cyanocobalamin ($B_{12}$) | 0.0084 mg/l | 0.0166 mg/l |
| | Nicotinamide | 66 mg/l | 132 mg/l |
| | Panthenol | 23.4 mg/l | 46.7 mg/l |
| | Folic acid | 0.667 mg/l | 1.334 mg/l |
| | L-Isoleucine | 8.0 g/l | 8.0 g/l |
| | L-Leucine | 14.0 g/l | 14.0 g/l |
| | L-Lysine acetate | 14.8 g/l | 14.8 g/l |
| | L-Methionine | 3.9 g/l | 3.9 g/l |
| | L-Phenylalanine | 7.0 g/l | 7.0 g/l |
| | L-Threonine | 5.7 g/l | 5.7 g/l |
| | L-Tryptophan | 2.0 g/l | 2.0 g/l |
| | L-Valine | 8.0 g/l | 8.0 g/l |
| | L-Alanine | 8.0 g/l | 8.0 g/l |
| | L-Arginine | 10.5 g/l | 10.5 g/l |
| | L-Aspartic acid | 1.0 g/l | 1.0 g/l |
| | L-Cysteine | 1.0 g/l | 1.0 g/l |
| | L-Glutamic acid | 1.0 g/l | 1.0 g/l |
| | L-Histidine | 5.0 g/l | 5.0 g/l |
| | L-Proline | 5.0 g/l | 5.0 g/l |
| | L-Serine | 3.0 g/l | 3.0 g/l |
| | L-Tyrosine | 0.5 g/l | 0.5 g/l |
| | Glycine | 5.9 g/l | 5.9 g/l |
| | Sodium citrate | 0.97 g/l | 0.97 g/l |
| | Potassium acetate | 1.15 g/l | 1.15 g/l |
| | Potassium phosphate | 2.61 g/l | 2.61 g/l |
| Solution (C) | Retinol palmitate (A) | 412500 IU/l | 825000 IU/l |
| | Cholecalciferol ($D_3$) | 25000 IU/l | 50000 IU/l |
| | Tocopherol acetate (E) | 1.25 g/l | 2.5 g/l |
| | Phytonadione (K) | 0.25 g/l | 0.5 g/l |
| | Sodium riboflavin phosphate ($B_2$) | 0.575 g/l | 1.150 g/l |
| | Ascorbic acid (C) | 12.5 g/l | 25.0 g/l |

Example 3

Solution (C) (4 ml) prepared in Example 1 was charged into each of holders made of the materials shown in Table 3, to thereby obtain a holder which contains a solution of vitamin $D_3$. Each of these holders containing a solution of vitamin $D_3$ was subjected to autoclaving and wrapped in a nylon multi-layered-film bag together with a deoxidizing agent (trade name: Ageless, product of Mitsubishi Gas Chem. Co., Inc.). The thus-wrapped holders were allowed to stand at 40° C. for four months. Thereafter, the content of each vitamin in each holder was measured through HPLC. The results are shown in Table 3. The content of each vitamin is represented by a percentage (%) of the initially incorporated amount.

TABLE 3

| | | | No. 1 | No. 2 | No. 3 | No. 4 | No. 5 |
|---|---|---|---|---|---|---|---|
| Holder | Material | | Poly-ethylene | Poly-ethylene | Poly-propylene | Poly-ethylene | Poly-propylene |
| | Thickness (μm) | | 30 | 100 | 30 | 250 | 250 |
| | Area of solution-containing portion ($cm^2$) | | 16 | 16 | 16 | 32 | 32 |
| | Volume of resin ($cm^3$) | | 0.048 | 0.12 | 0.048 | 0.8 | 0.8 |
| | Volume of resin ($cm^3$)/ Vitamin D (1 μmol) | | 7.4 | 18.5 | 7.4 | 123.2 | 123.2 |
| Vitamin content (%) | Vitamin A | After sterilization | 91.1 | 90.9 | 90.7 | 89.1 | 88.9 |
| | | 40° C., 4 months | 80.7 | 81.3 | 81.2 | 78.3 | 77.8 |
| | Vitamin E | After sterilization | 98.7 | 99.4 | 97.6 | 98.2 | 97.6 |
| | | 40° C., 4 months | 98.3 | 99.7 | 97.3 | 95.6 | 95.3 |
| | Vitamin K | After sterilization | 95.4 | 94.7 | 96.1 | 94.3 | 93.9 |
| | | 40° C., 4 months | 91.3 | 90.8 | 91.3 | 89.1 | 88.7 |
| | Vitamin $B_2$ | After sterilization | 94.8 | 96.3 | 95.4 | 94.6 | 95.3 |
| | | 40° C., 4 months | 90.7 | 91.2 | 91.0 | 90.9 | 91.2 |
| | Vitamin C | After sterilization | 96.2 | 97.1 | 97.3 | 97.5 | 96.8 |
| | | 40° C., 4 months | 94.3 | 95.4 | 94.2 | 94.8 | 93.1 |
| | Vitamin $D_3$ | After sterilization | 95.4 | 94.6 | 96.2 | 89.8 | 87.5 |
| | | 40° C., 4 months | 86.2 | 81.3 | 85.8 | 66.3 | 69.1 |

The results shown in Table 3 indicate that the content of each vitamin in the holders Nos. 1 through 3 (in the scope of the present invention) falls within the acceptable range even after been left for 4 months.

In contrast, in the holders Nos. 4 and 5, the content of vitamin $D_3$ fell outside the acceptable range.

Examples 4 and 5

In the same manner as in Example 1, solution (A), solution (B), and solution (C) having the compositions shown in Table 4 were prepared. In a holder produced from a three-layered film (the thickness of each layer: 10 μm) in which the outer and the inner layers are made of polyethylene and the intermediate layer is made of ethylene.tetracyclododecene copolymer (trade name: Apel, product of Mitsui Chemicals, Inc.), solution (C) (4 ml) was charged and the inlet was melt-sealed. In a two-compartment container, the prepared holder was attached to one of the compartments. Solution (A) (600 ml) and solution (B) (300 ml) were charged into two compartments separately, and the container was sealed, autoclaved, and wrapped, in the same manner as in Example 1.

TABLE 4

| | Ingredient | Example 4 | Example 5 |
|---|---|---|---|
| Solution (A) | Glucose | 292 g/l | 292 g/l |
| | Sodium chloride | 2.83 g/l | 2.83 g/l |
| | Magnesium sulfate | 1.23 g/l | 1.23 g/l |
| | Calcium chloride | 0.73 g/l | 0.73 g/l |
| | Zinc sulfate | 9.6 mg/l | 9.6 mg/l |
| | Thiamin hydrochloride ($B_1$) | 3.25 mg/l | 13.0 mg/l |
| | Pyridoxine hydrochloride ($B_6$) | 4.08 mg/l | 12.3 mg/l |
| | Panthenol | 11.7 mg/l | 25 mg/l |
| Solution (B) | L-Isoleucine | 8.0 g/l | 8.0 g/l |
| | L-Leucine | 14.0 g/l | 14.0 g/l |
| | L-Lysine acetate | 14.8 g/l | 14.8 g/l |
| | L-Methionine | 3.9 g/l | 3.9 g/l |

TABLE 4-continued

| | Ingredient | Example 4 | Example 5 |
|---|---|---|---|
| | L-Phenylalanine | 7.0 g/l | 7.0 g/l |
| | L-Threonine | 5.7 g/l | 5.7 g/l |
| | L-Tryptophan | 2.0 g/l | 2.0 g/l |
| | L-Valine | 8.0 g/l | 8.0 g/l |
| | L-Alanine | 8.0 g/l | 8.0 g/l |
| | L-Arginine | 10.5 g/l | 10.5 g/l |
| | L-Aspartic acid | 1.0 g/l | 1.0 g/l |
| | L-Cysteine | 1.0 g/l | 1.0 g/l |
| | L-Glutamic acid | 1.0 g/l | 1.0 g/l |
| | L-Histidine | 5.0 g/l | 5.0 g/l |
| | L-Proline | 5.0 g/l | 5.0 g/l |
| | L-Serine | 3.0 g/l | 3.0 g/l |
| | L-Tyrosine | 0.5 g/l | 0.5 g/l |
| | Glycine | 5.9 g/l | 5.9 g/l |
| | Sodium citrate | 0.97 g/l | 0.97 g/l |
| | Potassium acetate | 1.15 g/l | 1.15 g/l |
| | Potassium phosphate | 2.61 g/l | 2.61 g/l |
| | Folic acid | 0.667 mg/l | 0.667 mg/l |
| | Cyanocobalamin ($B_{12}$) | 0.0084 mg/l | 0.0168 mg/l |
| | Nicotinamide | 66 mg/l | 200 mg/l |
| Solution (C) | Retinol palmitate (A) | 412500 IU/l | 825000 IU/l |
| | Cholecalciferol ($D_3$) | 25000 IU/l | 50000 IU/l |
| | Tocopherol acetate (E) | 1.25 g/l | 2.5 g/l |
| | Phytonadione (K) | 0.25 g/l | 0.5 g/l |
| | Sodium riboflavin phosphate ($B_2$) | 0.575 g/l | 1.15 g/l |
| | Ascorbic acid (C) | 12.5 g/l | 50 g/l |
| | Biotin | 7.5 mg/l | 15 mg/l |

The above-described transfusion fluid containers in Examples 4 and 5 were allowed to stand at 40° C. for four months after autoclaving. Thereafter, the contents of vitamins in the containers were measured through a bioassay according to Pharmacopoeia of Japan (for vitamin $B_{12}$ and biotin) or through HPLC (for other vitamins). The results are shown in Table 5. The content of each vitamin is represented by a percentage (%) of the initially incorporated amount.

TABLE 5

| | Example 4 | | Example 5 | |
|---|---|---|---|---|
| | Immediately after sterilization | 40° C., 4 months | Immediately after sterilization | 40° C., 4 months |
| Thiamin hydrochloride ($B_1$) | 93.8 | 87.4 | 93.5 | 86.6 |
| Pyridoxine hydrochloride ($B_6$) | 100.5 | 100.1 | 99.7 | 99.8 |
| Cyanocobalamin ($B_{12}$) | 91.3 | 89.2 | 96.5 | 90.5 |
| Nicotinamide | 98.6 | 97.8 | 98.2 | 98.5 |
| Panthenol | 97.4 | 96.9 | 98.5 | 97.6 |
| Biotin | 100.4 | 99.8 | 98.7 | 100.3 |
| Folic acid | 97.8 | 97.5 | 98.3 | 99.1 |
| Retinol palmitate (A) | 87.2 | 84.5 | 86.5 | 83.9 |
| Cholecalciferol ($D_3$) | 89.8 | 88.7 | 90.1 | 89.6 |
| Tocopherol acetate (E) | 94.9 | 95.1 | 95.3 | 94.8 |
| Phytonadione (K) | 96.2 | 95.3 | 95.8 | 95.4 |
| Sodium riboflavin phosphate ($B_2$) | 86.5 | 83.2 | 85.9 | 84.3 |
| Ascorbic acid (C) | 98.7 | 98.3 | 97.8 | 97.5 |

The results shown in Table 5 indicate that in the transfusion fluid containers of the present invention, the vitamin contents of 13 species of vitamins fell within the acceptable range (≧80%) even after been left for four months.

INDUSTRIAL APPLICABILITY

The vitamin D solution holder of the present invention can minimize adsorption of vitamin D to the holder, and therefore the content of vitamin D can be maintained to fall within an acceptable range.

What is claimed is:

1. A holder for a Vitamin D solution, comprising:

a solution holding portion defined by a walled enclosure comprising walls made of a polyolefin, wherein the walls of the walled enclosure have an inside surface area facing an interior of the solution holding portion and a wall thickness; and a Vitamin D solution comprising Vitamin D or a derivative thereof contained in the solution holding portion;

wherein the walls of the walled enclosure have a volume, calculable by multiplying the inside surface area of the walls of the walled enclosure by the wall thickness of the walls of the walled enclosure, of not greater than 30 $cm^3$ per μmol of Vitamin D or the derivative thereof in the Vitamin D solution.

2. The holder according to claim 1, wherein the walls of the walled enclosure have a volume of not greater than 20 $cm^3$ per μmol of Vitamin D or the derivative thereof in the Vitamin D solution.

3. The holder according to claim 1, wherein the walls of the walled enclosure have a volume of not greater than 10 $cm^3$ per μmol of Vitamin D or the derivative thereof in the Vitamin D solution.

4. The holder according to claim 1, wherein the wall thickness is not greater than 100 μm.

5. A holder for a Vitamin D solution, comprising:

a solution holding portion defined by an enclosure having a multi-layer structure; and a Vitamin D solution comprising Vitamin D or a derivative thereof contained in the solution holding portion;

wherein the multi-layer structure comprises an inner layer comprising a polyolefin having an inside surface area in contact with the Vitamin D solution and a thickness, and an outer layer comprising a polyolefin outside of the inner layer in a direction away from the Vitamin D solution;

wherein the inner layer has a volume, calculable by multiplying the inside surface area of the inner layer by the thickness of the inner layer, of not greater than 30 $cm^3$ per μmol of Vitamin D or the derivative thereof in the Vitamin D solution.

6. The holder according to claim 5, wherein the outer layer further comprises a resin that does not substantially absorb any Vitamin D.

7. A holder for a Vitamin D solution, comprising:

a solution holding portion defined by an enclosure having a multi-layer structure; and a Vitamin D solution comprising Vitamin D or a derivative thereof contained in the solution holding portion;

wherein the multi-layer structure comprises an inner layer having an inside surface area in contact with the Vitamin D solution and a thickness, an outer layer outside the inner layer in a direction away from the Vitamin D solution, and an intermediate layer between the inner layer and the outer layer;

wherein the inner layer has a volume, calculable by multiplying the inside surface area of the inner layer by the thickness of the inner layer, of not greater than 30 $cm^3$ per μmol of Vitamin D or the derivative thereof in the Vitamin D solution; and wherein the inner layer comprises a polyolefin, the intermediate layer comprises a cyclic olefin copolymer, and the outer layer comprises a polyolefin.

8. A transfusion fluid container, comprising:

a holder having a solution holding portion defined by a walled enclosure comprising walls made of a polyolefin, wherein the walls of the walled enclosure have an inside surface area facing an interior of the solution holding portion and a wall thickness; and a Vitamin D solution comprising Vitamin D or a derivative thereof contained in the solution holding portion;

wherein the walls of the walled enclosure have a volume, calculable by multiplying the inside surface area of the walls of the walled enclosure by the wall thickness of the walls of the walled enclosure, of not greater than 30 $cm^3$ per μmol of Vitamin D or the derivative thereof in the Vitamin D solution; and wherein the transfusion fluid container further comprises a first flexible compartment isolated from the holder.

9. The transfusion fluid container according to claim 8, comprising a material that is the same as that used for the holder for the Vitamin D solution or a material that is the same as that used in an outermost layer of the holder; and an edge of a peripherally sealed portion of the holder for the Vitamin D solution sandwiched between peripheral portions of the container.

10. The transfusion fluid container according to claim 8, comprising a second compartment divided from the first compartment by a partition that allows fluid communication therethrough, in which solution (B) comprising amino acids, is contained in one of the first and second compartments, solution (A) comprising a reducing sugar, is contained in the other of the first and second compartments, and the holder for the Vitamin D solution is accommodated in either one of the first and second compartments.

11. The transfusion fluid container according to claim 10, wherein solution (A) further comprises Vitamin B1, solution (B) further comprises folic acid, and the Vitamin D solution further comprises other fat-soluble vitamins and Vitamin C, wherein Vitamin B2 is incorporated into solution (B) or the Vitamin D solution and the pHs of solution (A), solution (B) and the Vitamin D solution are adjusted to 3.5–4.5, 5.0–7.0 and 5.0–7.0, respectively.

12. The transfusion fluid container according to claim 11, wherein solution (A) further comprises a pantothenic acid derivative, and Vitamin B2 is incorporated into the Vitamin D solution.

13. The transfusion fluid container according to claim 11, wherein solution (B) further comprises Vitamin B12.

14. The transfusion fluid container according to claim 11, wherein solution (A) further comprises Vitamin B6, solution (B) further comprises a nicotinic acid derivative, and the Vitamin D solution further comprises biotin.

15. The transfusion fluid container according to claim 11, wherein the fat-soluble vitamin contained in the Vitamin D solution is solubilized therein by a surfactant.

16. The transfusion fluid container according to claim 11, wherein an electrolyte is incorporated into at least one of solution (A), solution (B) and the Vitamin D solution.

17. A holder, comprising:

a first wall;

a second wall opposing the first wall and sealed to the first wall about a perimeter so as to form an enclosed chamber within the perimeter; and a Vitamin D solution comprising Vitamin D or a derivative thereof contained in the chamber; wherein the first wall comprises a first resin layer comprising a polyolefin having a first surface area that is in contact with the Vitamin D solution in the chamber and a first thickness;

the second wall comprises a second resin layer comprising a polyolefin opposing the first resin layer and having a second surface area that is in contact with the Vitamin D solution in the chamber and a second thickness;

a volume of the first resin layer is calculable by multiplying the first surface area by the first thickness;

a volume of the second resin layer is calculable by multiplying the second surface area by the second thickness; and wherein a sum of the volume of the first resin layer and the second resin layer is not greater than 30 $cm^3$ per $\mu$mol of Vitamin D or the derivative thereof in the Vitamin D solution.

18. The holder according to claim 17, wherein:

the first wall comprises a multi-layer structure, including a first inner layer in contact with the Vitamin D solution in the chamber and a first outer layer outside the first inner layer in a direction away from the chamber, and wherein the first resin layer is the first inner layer;

the second wall comprises a multi-layer structure, including a second inner layer in contact with the Vitamin D solution in the chamber and a second outer layer outside the second inner layer in a direction away from the chamber, and wherein the second resin layer is the second inner layer; and the first and second outside layers further comprise a resin that does not substantially absorb any Vitamin D.

19. The holder according to claim 17, wherein the thickness of the first resin layer is no greater than 100 $\mu$m and the thickness of the second resin layer is no greater than 100 $\mu$m.

20. The holder according to claim 17, wherein:

the first wall comprises a multi-layer structure, including a first inner layer in contact with the Vitamin D solution in the chamber, a first outer layer outside the first inner layer in a direction away from the chamber, and a first intermediate layer between the first inner layer and the first outer layer, and wherein the first resin layer is the first inner layer;

the second wall comprises a multi-layer structure, including a second inner layer in contact with the Vitamin D solution in the chamber, a second outer layer outside the second inner layer in a direction away from the chamber, and a second intermediate layer between the second inner layer and the second outer layer, and wherein the second resin layer is the second inner layer; and the first and second inner layers comprise a polyolefin, the first and second intermediate layers comprise a cyclic olefin copolymer, and the first and second outer layers comprise a polyolefin.

* * * * *